US005843400A

United States Patent [19]
Fujibayashi et al.

[11] Patent Number: 5,843,400
[45] Date of Patent: Dec. 1, 1998

[54] DIAGNOSTIC AGENT FOR HYPOXIA OR MITOCHONDRIAL DYSFUNCTION COMPRISING RADIOACTIVE COPPER COMPLEX OF DITHIOSEMICARBAZONE DERIVATIVE OR DIAMINE DIOL SCHIFF BASE DERIVATIVE

[75] Inventors: Yasuhisa Fujibayashi, Kyoto-fu; Akira Yokoyama, Shiga-ken, both of Japan

[73] Assignee: Nihon Medi-Physics Co., Ltd., Hyogo-ken, Japan

[21] Appl. No.: 584,300

[22] Filed: Jan. 11, 1996

[30] Foreign Application Priority Data

Jan. 9, 1995 [JP] Japan ................................ 7-017504

[51] Int. Cl.$^6$ ........................... A61K 51/00; A61M 36/14
[52] U.S. Cl. ........................... 424/1.65; 564/36; 564/19; 424/1.11
[58] Field of Search ................................... 424/1.11, 1.65, 424/9.1, 9.3, 9.323, 9.36, 9.4, 9.42; 534/10; 564/1, 18, 19, 36

[56] References Cited

U.S. PATENT DOCUMENTS

| | | | |
|---|---|---|---|
| 4,795,626 | 1/1989 | Deutsch et al. | 424/1.65 |
| 4,915,931 | 4/1990 | Yokoyama et al. | 424/1.65 |
| 4,917,879 | 4/1990 | Deutsch et al. | 534/10 |
| 5,071,636 | 12/1991 | Yamauchi et al. | 534/10 |
| 5,079,346 | 1/1992 | Kung | 534/10 |

OTHER PUBLICATIONS

Mathias et al (Aug. 1995), J. Nucl. Med, vol. 36, No. 8, pp. 1451–1455, "Species–Dependent Binding of Copper (II) Bis(Thiosemicarbazone) Radiopharmaceuticals to Serum Albumin".

Pastakia et al (1980), J. Nucl. Med, vol. 21, No. 1, pp. 67–70, "Tissue Distribution of Copper Labeled 3–ethoxy–2–oxobutyraldehyde bis (thiosemicarbazone) (Cu–64KTS) in Mice and Rats: Concise Communication".

Kagwanja et al (1994). Polyhedron, vol. 13, No. 18, pp. 2615–2627 Formation of Trimetallic Complexes Containing Redox–Active Nitrosyl Molybdenum Tris (3,5–dimethylpyrazolyl)–borato groups.

Green (1987), Nucl. Med. Biol., vol. 14, No. 1, pp. 59–61, "A Potential Copper Radiopharmaceutical for Imaging the Heart and Brain: Copper–Labeled Pyruvaldehyde Bis ($N^4$–methylthiosemicarbazone".

John et al (1994). Journal of Pharmaceutical Sciences, vol. 83, No. 4, pp. 587–590,"Preparation and Biodstribution of Copper–67 Complexes with Tetradentate Schiff–Base Ligands".

Deutsch et al (1987), J. Nucl. Med., vol. 28, No. 12, pp. 1870–1880, Development of Non–reducible Technetium–99m (III) cations as Myocardial Perfusion Imaging Agents: Initial Experience in Humans.

Geison et al (1994), J. Nucl. Med., vol. 35, No. 10., pp. 1698–1706, "Myocardial Uptake and Kinetic Properties of Technetium–99m–Q3 in Dogs".

Taniuchi et al (1995), Biol. Pharm. Bull., Vol. 18, No. 8, pp. 1126–1129, Cu–Pyruvaldehyde–bis ($N^4$–methylthiosemicarbazone) (Cu–PTSM), a Metal Complex with Selective NADH–Dependent Reduction by Complex I in Brain Mitochondria: A Potential Radiopharmaceutical for Mitochondria–Functional Imaging with Positron Emission Tomography.

John et al (1990), J. Med. Chem, vol. 33, No. 6, pp. 1764–1770, Structure Activity Relationships for Metal Labeled Blood Flow Tracers: Comparison of Keto Aldehyde Bis(thiosemicarbazonato) Copper II Derivatives.

Fujibayashi, et al (1993), Biol. Pharm. Bull., vol. 16, No. 2, pp. 146–149 "Mitochondria Selective Reduction of $^{62}Cu$–Pyruvaldehyde Bis ($N^4$–methylthiosemicarbazone) ($^{62}Cu$–PTSM) in the Murine Brain; a Novel Radiopharmaceutical for Brain Positron Emission Tomography (PET) Imaging".

K. Wada et al., "CU–ATSM, an Intracellular–Accessible Superoxide Dismutase (SOD)–Like Copper Complex: Evaluation in an Ischemia–Reperfusion Injury Model", *Biol. Pharm. Bull.*, vol. 17, No. 5, May 1994, pp. 701–704.

K. Wada et al., "Effects of Ischemia–reperfusion Injury on Myocardial Single Pass Extraction and Retention of CU–PTSM in Perfused Rat Hearts: Comparison with $^{201}Tl$ and $^{14}C$–Iodoantipyrine", *Nucl. Med. Biol.*, vol. 21, No. 4, 1994, pp. 613–617.

E.K. John et al., "Preparation and Biodistribution of Copper–67 Complexes with Tetradentate Schiff–Base Ligands", *Journal of Pharmaceutical Sciences*, vol. 83, No. 4, Apr. 1994, pp. 587–590.

Journal of Nuclear Medicine, New York, NY, US, vol. 29, No. 9, Sep. 1988, pp. 1549–1557, Green, M.A. et al: "Copper (II) Bis(Thiosemicarbazone) Complexes as Potential Tracers for Evaluation of Cerebral and Myocardial Blood Flow with Pet".

Journal of Medicinal Chemistry, vol. 33, 1990, Washington US, pp. 1764–1770, E.K. John et al,: "Structure–Activity Relationships for Metal–Labeled Blood Flow Tracers: Comparision of Keto Aldehyde Bis(Thiosemicarbazonato)Copper(II) Derivatives".

Chemical Abstracts, vol. 119, No. 19, 8 Nov. 1993, Columbus, Ohio, US; abstract No. 198662, Yokoyama, A. et al: "Basic research on the development of radioactive–copper labeled radiopharmaceuticals" *abstract* & Kyoto Daigaku Genshiro Jikkensho, [Tech. Rep.](1992), Kurri–TR–366, 91–2 Coden: KDGHDH;ISSN: 0287–9808, 1992.

Journal of Nuclear Medicine, vol. 36, No. 5, May 1995, New York US, p. 49P, Y. Yonekura et al: "New Nonnitroimidazole Hypoxia Imaging Agents, CU–62–Dithiosemicarbazone Complexes with Low Redoxpotential"(abstract No. 197).

*Primary Examiner*—John Kight
*Assistant Examiner*—Dameron Jones
*Attorney, Agent, or Firm*—Sughrue, Mion, Zinn, Macpeak & Seas, PLLC

[57] ABSTRACT

A diagnostic agent for hypoxia or mitochondrial dysfunction is disclosed, comprising a radioactive copper complex of a dithiosemicarbazone derivative or a radioactive copper complex of a diamine diol schiff base derivative. This agent has good transferability to the target tissue, reduction reaction affinity at a hypoxic site, high stability in a non-target site and rapidly disappears.

11 Claims, 4 Drawing Sheets

DIAGNOSTIC AGENT FOR HYPOXIA OR MITOCHONDRIAL DYSFUNCTION COMPRISING RADIOACTIVE COPPER COMPLEX OF DITHIOSEMICARBAZONE DERIVATIVE OR DIAMINE DIOL SCHIFF BASE DERIVATIVE

BACKGROUND OF THE INVENTION

1. Field of the Invention

The present invention relates to a diagnostic agent for hypoxia or mitochondrial dysfunction comprising a radioactive copper complex of a dithiosemicarbazone derivative or a radioactive copper complex of diamine diol schiff base derivative, particularly to a pharmaceutical useful for the detection of a hypoxic site or a site of mitochondrial dysfunction in brain, myocardia, tumor tissues and so on.

2. Background Information

Existence of a hypoxic site or a site of mitochondrial dysfunction has been noted in hypoxic diseases in brain and myocardia or in certain kinds of tumors. It is believed that, in these sites, an electron-excess state generated by hypoxic condition or mitochondrial dysfunction due to a high energy demand and a blood flow depression is present. Detection of such a hypoxic site or a site of mitochondrial dysfunction is important for the initiation of a therapy of tissues in the condition of hypoxia or mitochondrial dysfunction maintaining suitable metabolic function in ischemic brain or myocardial disease or for the decision of use of a radiosensitizer aiming at the improvement of radiosensitivity of a hypoxic tumor in certain kinds of tumors. Many attempts have heretofore been made in this field to develop hypoxia-detecting radioactive pharmaceuticals having a nitroimidazole group. The conventional radioactive pharmaceuticals having a nitroimidazole group as the basic structure have been fundamentally originated from a viewpoint that they are prepared as labelled compound using a compound developed as a radiosensitizer. The most important problem of the radiosensitizer is their neurotoxicity and the development of said radioactive pharmaceuticals has been directed to those having a decreased fat solubility and hence decreased transferability to cells in order to reduce the problem. It is important that radioactive pharmaceuticals have properties that it is incorporated rapidly in cells, is accumulated in hypoxic sites and disappear rapidly from normal sites, because radioactive pharmaceuticals is applied at very small dosage. As seen in the conventional attempts, however, if the designing concept of radioactive pharmaceuticals of which cell-membrane permeability is reduced is used to design hypoxia-detecting radioactive pharmaceuticals, said hypoxia-detecting radioactive pharmaceuticals inevitably have difficulty of transferability to cells, disappear slowly from normal cells and no improvement can be expected for selectivity between targeted and normal cells.

Numerous F-18 labeled compounds have also been proposed as substances having good transferability to cells and ability of disappearance from normal cell. However, the production of them needs a in-hospital cyclotron facility and therefore they can not find wide application. Thus, the conventionally proposed hypoxia-detecting radioactive pharmaceuticals have problems in selectivity or wide-applicability and have not been practically used. Besides, no mitochondrial dysfunction detecting radioactive pharmaceuticals have been known.

In recent years, the Zn-62/Cu-62 generator has been developed, which allows easy production of Cu-62, a positron nuclide, in the form of a glycine complex. Therefore, the production of positron radio nuclide labeled substance has become possible without using in-hospital cyclotron facility.

Under such circumstances, the present invention intends to provide a diagnostic agent for hypoxia or mitochondrial dysfunction as a detector for hypoxia or mitochondrial dysfunction having a good transferability to the target tissues, an affinity to reductive reaction in said target tissues, a high stability in non-target tissues and rapid disappearance therefrom.

The present inventors have conducted extensive studies from the viewpoint that, in order to detect a hypoxic site or a site of mitochondrial dysfunction, it is essential that an organic compound having a very low oxidation-reduction potential receives an electron only in cells of electron excess state and stays there and, as the result, have found the facts that some copper complexes of dithiosemicarbazone derivative or some copper complexes of diamine diol schiff base derivative have a high transferability to brain, myocardium and the like on the one hand, are rapidly transfered to outside of cells without being reduced in a normal mitochondrion because of its very low oxidation-reduction potential and show a significant difference in staying ability in myocardia between anoxia and oxygen-containing perfusates in a perfused myocardial model of rat on the other hand, which facts lead them to the present invention.

SUMMARY OF THE INVENTION

Accordingly, the present invention relates to a diagnostic agent for hypoxia or mitochondrial dysfunction comprising a radioactive copper complex of a dithiosemicarbazone derivative (hereinafter, abbreviated as Cu-62-DTS) represented by the following formula:

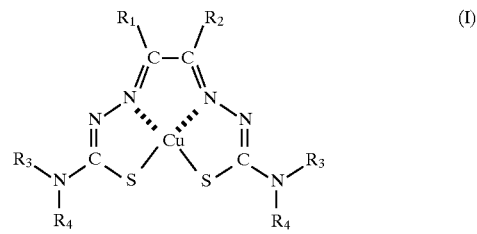

wherein each of $R_1$, $R_2$, $R_3$ and $R_4$ independently represents hydrogen, alkyl or alkoxy, and Cu represents a radioactive isotope Cu-62, or a radioactive copper complex of a diamine diol schiff base derivative (hereinafter, abbreviated as Cu-62-DDS) represented by the following formulae:

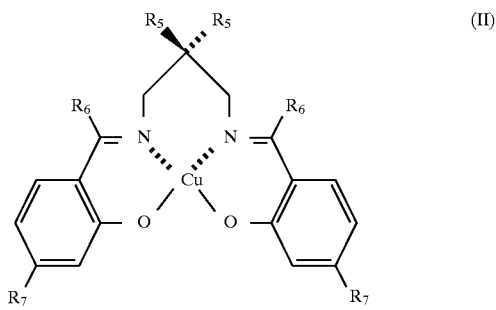

wherein each of $R_5$, $R_6$, and $R_7$ independently represents hydrogen, alkyl or alkoxy, and Cu represents a radioactive isotope Cu-62, or

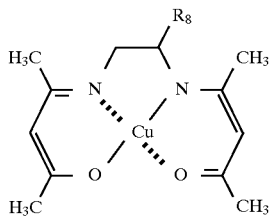

(III)

wherein $R_8$ represents hydrogen or alkyl, and Cu represents a radioactive isotope Cu-62.

PREFERRED EMBODIMENTS

Figure 1:
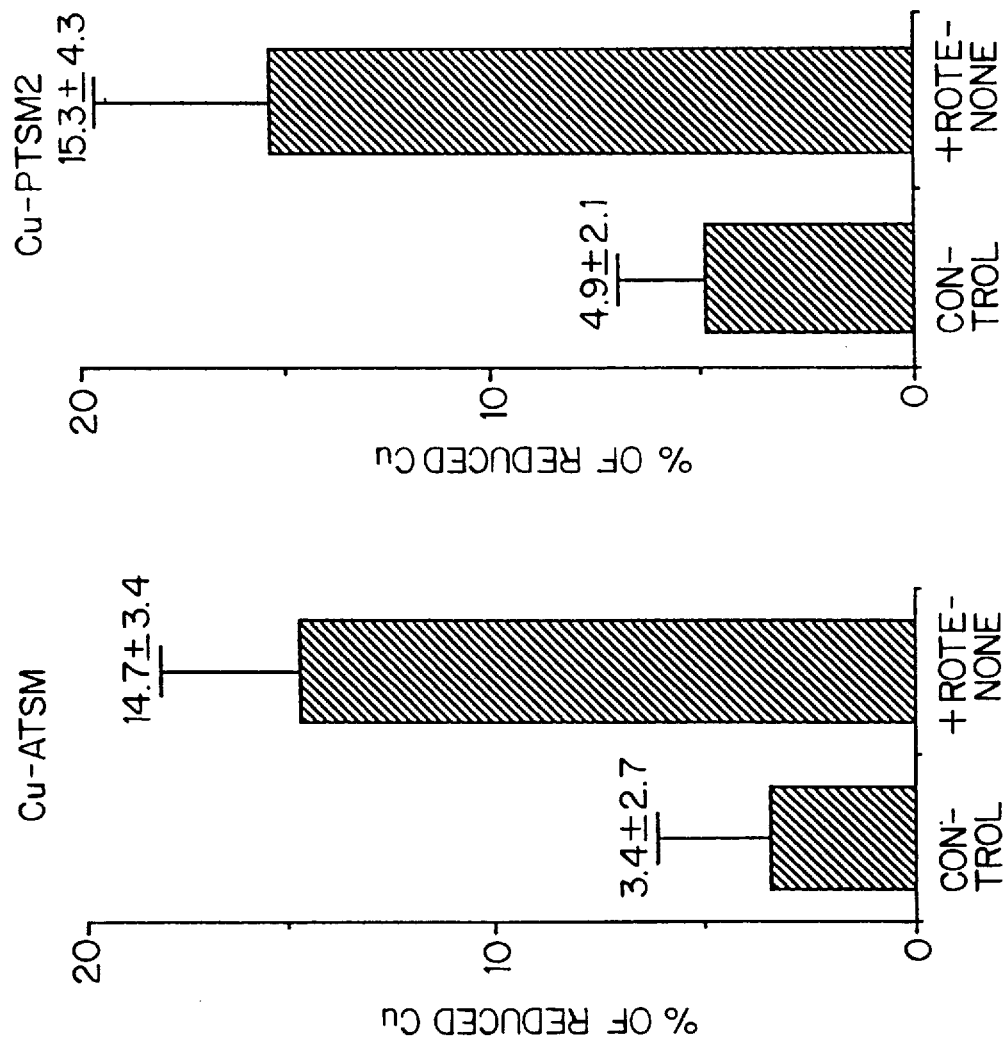
FIG. 1 is a bar graph demonstrating the effect of inhibition of the mitochondrial electron transport system on the reduction of Cu-ATSM and Cu-PTSM2.

In the definitions for the substituents $R_1$, $R_2$, $R_3$ and $R_4$ in the compound (I), each of the alkyl and the alkoxy has carbons of usually 1–5 and preferably 1–3. Specifically, examples of the compound (I) include Cu-62-glyoxal bis(N4-methylthiosemicarbazone) (hereinafter, abbreviated as Cu-62-GTSM), Cu-62-glyoxal bis(N4-dimethylthiosemicarbazone) (hereinafter, abbreviated as Cu-62-GTSM2), Cu-62-ethylglyoxal bis(N4-methylthiosemicarbazone) (hereinafter, abbreviated as Cu-62-ETSM), Cu-62-ethylglyoxal bis(N4-ethylthiosemicarbazone) (hereinafter, abbreviated as Cu-62-ETSE), Cu-62-pyruvaldehyde bis(N4-methylthiosemicarbazone) (hereinafter, abbreviated as Cu-62-PTSM), Cu-62-pyruvaldehyde bis(N4-dimethylthiosemicarbazone) (hereinafter, abbreviated as Cu-62-PTSM2), Cu-62-pyruvaldehyde bis(N4-ethylthiosemicarbazone) (hereinafter, abbreviated as Cu-62-PTSE), Cu-62-diacetyl bis(N4-methylthiosemicarbazone) (hereinafter, abbreviated as Cu-62-ATSM), Cu-62-diacetyl bis(N4-dimethylthiosemicarbazone) (hereinafter, abbreviated as Cu-62-ATSM2), Cu-62-diacetyl bis(N4-ethylthiosemicarbazone) (hereinafter, abbreviated as Cu-62-ATSE), and the like. Among them, Cu-62-ATSM or Cu-62-PTSM2 are preferred embodiments.

In the definition for the substituents $R_5$, $R_6$ and $R_7$ in the compound (II), each of the alkyl and alkoxy has carbons of usually 1–5, and preferably 1–3. Examples of the compound (II) include Cu-62-disalicylaldehyde-1,3-propanediamine (hereinafter, abbreviated as Cu-62-DSP), Cu-62-disalicylaldehyde-2,2-dimethyl-1,3-propanediamine (hereinafter, abbreviated as Cu-62-DSDP), Cu-62-di-4-methoxysalicylaldehyde-1,3-propanediamine (hereinafter, abbreviated as Cu-62-DMSP), and Cu-62-di-4-methoxysalicylaldehyde-2,2-dimethyl-1,3-propanediamine (hereinafter, abbreviated as Cu-62-DMSDP). Among them, Cu-62-DSDP is preferred embodiment.

In the definition for the substituent $R_8$ in the compound (III), the alkyl has carbons of usually 1–5, and preferably 1–3. Examples of the compound (III) include Cu-62-diacetylacetone ethylenediamine (hereinafter, abbreviated as Cu-62-DAED), Cu-62-diacetylacetone-1,2-propanediamine (hereinafter, abbreviated as Cu-62-DAPD), and the like. Among them, Cu-62-DAED is preferred embodiment.

The copper complexes of the dithiosemicarbazone derivative are prepared as follows: For example, as the method described in Petering et al. (Cancer Res., 1964, 24, 367–372), 1 mol of an α-ketoaldehyde in an aqueous solution or 50% ethanol solution is added dropwise to a solution containing 2.2 moles of thiosemicarbazide, N4-methylthiosemicarbazide, N4-dimethylthiosemicarbazide or the like and 5% of glacial acetic acid at 50°–60° C. over 30–40 minutes. The reaction solution is stirred during the course of the addition. After the addition is terminated, the reaction solution is allowed to stand at room temperature for several hours and crystals formed by cooling are separated. The crystals are dissolved in methanol and purified by recrystallization. The dithiosemicarbazone derivative thus obtained is dissolved in dimethylsulfoxide (DMSO) and contacted with a solution of copper nitrate according to the method described by Green et al. (Nucl. Med. Biol., 1987, 14, 59–61) to give a copper complex. Then, the dithiosemicarbazone derivative and Cu-62-glycine obtained by means of a Zn-62/Cu-62 generator (Fujibayashi et al.,J. Nucl. Med., 1989, 30, 1838–1842) are subjected to ligand exchange reaction according to the method described by Fujibayashi et al. (Nucl. Med. Biol., 1992, 19, 39–44) to give a Cu-62-DTS.

The ligand exchange reaction between Cu-62-glycine and pyruvaldehyde bis(N4-methylthiosemicarbazone) (hereinafter, abbreviated as PTSM) is conducted specifically in the following manner. Elution through a Zn-62/Cu-62 generator is carried out with an aqueous solution for injection containing 200 mM glycine as an eluent to give Cu-62-glycine complex in the form of a glycine solution. The obtained glycine solution of Cu-62-glycine complex is mixed with an ethanol solution or DMSO solution of PTSM at room temperature, whereby the ligand exchange reaction can be easily effected to give Cu-62-PTSM quantitatively. The radiochemical purity of Cu-62-PTSM thus obtained is 95% or above.

Cu-62-DDS can be obtained by synthesizing copper complex of diamine diol schiff base derivative in the same way as described in Chen D. et al. (Inorg. Chem. 1987, 26, 1026–1030; Inorg. Chem. 1989, 28, 2647–2652) and then conducting the ligand exchange reaction between the copper complex of diamine diol schiff base derivative thus obtained and Cu-62-glycine.

Extent of reduction of Cu by murine brain mitochondria was tested on Cu-ATSM which is non-radioactive coper complex and was obtained in the same way. It was shown that almost no reduction of Cu occurred in mitochondria of normal brain, but the reduction of Cu proceeded in mitochondria derived to an electron excess state similar to mitochondria in hypoxia or dysfunction by treating with rotenone, an electron transport system inhibitor, showing specific reduction by Cu-ATSM in an electron excess state. Such a specificity of reductive reaction were also observed in other non-radioactive Cu-DTS and Cu-DDS. This indicates that non-radioactive Cu-DTS and Cu-DDS are useful as a marker to find hypoxic state of tissues or mitochondrial dysfunction. Such a kind of behavior on oxygen is also true in compounds labeled with a radioisotope Cu-62.

Further, in a test using a perfused myocardial model of rat, Cu-62-ATSM disappeared rapidly from the myocardia in the presence of oxygen in the perfusate and, after 15 minutes of administration, decreased down to about 20% of the maximum value. When the perfusate of the same perfused myocardial model was changed to an anoxic perfusate and after about 10 minutes Cu-62-ATSM was administered again, it stayed at a high level. Further, when the perfusate was changed back to the original one and Cu-62-ATSM was administered, it showed the same staying curve as that of the original trial. Therefore, it is concluded that the state of oxygen concentration in the tissue can be estimated by examining Cu-62-ATSM concentration in the tissue because its staying in the tissue changes depending on the oxygen concentration.

The biodistribution of each Cu-62-DTS and Cu-62-DDS shows a characteristic accumulation behavior corresponding to the difference of their side chain. For example, Cu-62-PTSM showed a high transferability to brain as well as staying ability comparatively but Cu-62-PTSM showed heigher staying ability when the brain is abnormal. However, it was revealed that Cu-62-ATSM, Cu-62-PTSM2, Cu-62-ATSM2 and so on were transferred once to brain but rapidly disappeared therefrom, indicating that they did not have staying ability in the normal animal brain. Cu-62-ETSM, Cu-62-ETSE, Cu-62-PTSE, Cu-62-ATSE, Cu-62-DSDP, Cu-62-DAED and so on showed similar behavior. Thus, Cu-62-DTS and Cu-62-DDS have a property suitable for the detection of hypoxia in addition to the aforesaid transferability to brain and ability of being reduced only in the electron excess state. Furthermore, easier availability of labeled compounds with the positron nuclide Cu-62 allowed detection of transfer in extremely small quantities.

Cu-62-DTS and Cu-62-DDS may be used as a diagnostic agent by adjusting according to the following method. For example, to 0.2 ml of DMSO solution containing 0.1 mg of DTS, may be added aseptically 4 ml of glycine solution containing Cu-62-glycine complex having 5–20 mCi of radio activity and the mixture may be stirred several times to give a diagnostic agent. The amount of the diagnostic agent thus obtained is equal to one dose. The diagnostic agent of the present invention is useful for diagnosing hypoxia or mitochondrial dysfunction in brain, heart, tumor, and the other tissue. Examples of disease for the diagnostic agent of the present invention include encephalon infarction, ischemia cardiopathy, epilepsy, dementia, myocardial infarction, cardiomyopathy, myocardial adriamycin affection, tumor and so on.

The diagnosis of hypoxia or mitochondrial dysfunction may be done by administering an effectcive amount of 62-Cu-DTS or 62-Cu-DDS to a mammal and detecting the radioactive copper nuclide staying in the mammal body.

EXAMPLES

The present invention will be described in more detail with reference to the following Examples.

Example 1: Effects of mitochondrial electron transport inhibition on the reduction of Cu-DTS and Cu-DDS Brains of male ddY mice were homogenized in a Potter-Elevehjem type homogenizer at a concentration of 1.5 g/ml. The homogenate was centrifuged at 1,000×g for 5 minutes and the supernatant was further centrifuged at 10,000×g for 10 minutes to give a crude mitochondria fraction. The part of the mitochondria fraction was treated with rotenone, an electron transport system inhibitor, in order to place the mitochondria fraction in a state similar to hypoxia. The treatment with rotenone leads the mitochondrial electron transport system complex and its upper site to an electron excess state.

Extent of reduction of Cu-DTS and Cu-DDS was determined with an electron spin resonance spectrometry (ESR). To each 1.8 ml of a suspension of normal mitochondria and mitochondria treated with rotenone was added 0.2 ml of DMSO solution of 0.2 mM of Cu-DTS or Cu-DDS and the mixture was incubated at 37° C. for 15 minutes. 0.3 ml of the mixture was put in an ESR tube and subjected to measurement of ESR signals under cooling in liquid nitrogen. The measurement of ESR spectra was carried out using an X-band spectrometer JES-FE3XG manufactured by Japan Electron Optic Laboratory. Spectrometry conditions were 5 mW microwave power; 6.3 gauss modulation amplitude; 100 KHz modulation frequency; 9.25 GHz microwave frequency; 3300±500 gauss magnetic field. The mesurement was based on the intensity of signals. The results obtained on Cu-ATSM and Cu-PTSM2 are shown in FIG. 1, and those obtained on the others are shown in Table 1.

In Cu-ATSM as an example, almost no reduction of Cu occurred in the normal mitochondria but the reduction of Cu proceeded in the mitochondria treated with rotenone, indicating the specific reduction of Cu-ATSM in the electron excess state. The specific reduction was also found in other Cu-DTS and Cu-DDS. Though Cu-DTS and Cu-DDS which are non-radioactive copper complex were examined in Example 1, it is expected that Cu-62-DTS and Cu-62-DDS which are radioactive one also show same behavior with the non-radioactive one.

Example 2: Effect of oxygen on the staying of Cu-62-DTS and Cu-62-DDS in myocardia in the perfused myocardial model Tests were performed on Cu-62-ATSM, Cu-62-PTSM2 and Cu-62-PTSM as Cu-62-DTS and Cu-62-DAED as Cu-62-DDS obtained in the above described manner. The perfused myocardial model of rat was prepared by the method of Langendorff's method. A male Wistar rat was injected intraperitoneally with 500 i.u. of heparin and the heart was isolated. The heart was washed with cold perfusate. The aorta was attached to a stainless cannula and the heart was perfused, immediately. The perfusate used was a Krebs-Ringer's bicarbonate solution at 37° C. and flowed at a rate of 6 ml/min. The perfusate was used after saturating with 95% oxygen+5% carbon dioxide or 95% nitrogen+5% carbon dioxide when occasion demanded. Each of the solution of Cu-62-DTS and Cu-62-DDS was administered as a bolus to the perfused myocardial model with a six-direction bulb injector. A BGO detector shielded with lead block was placed on the heart and the radioactivity in the myocardia was continuously measured. The values were corrected relating to the half-life and plotted taking the maximum value as 100 to give a retention curve.

Figure 2:
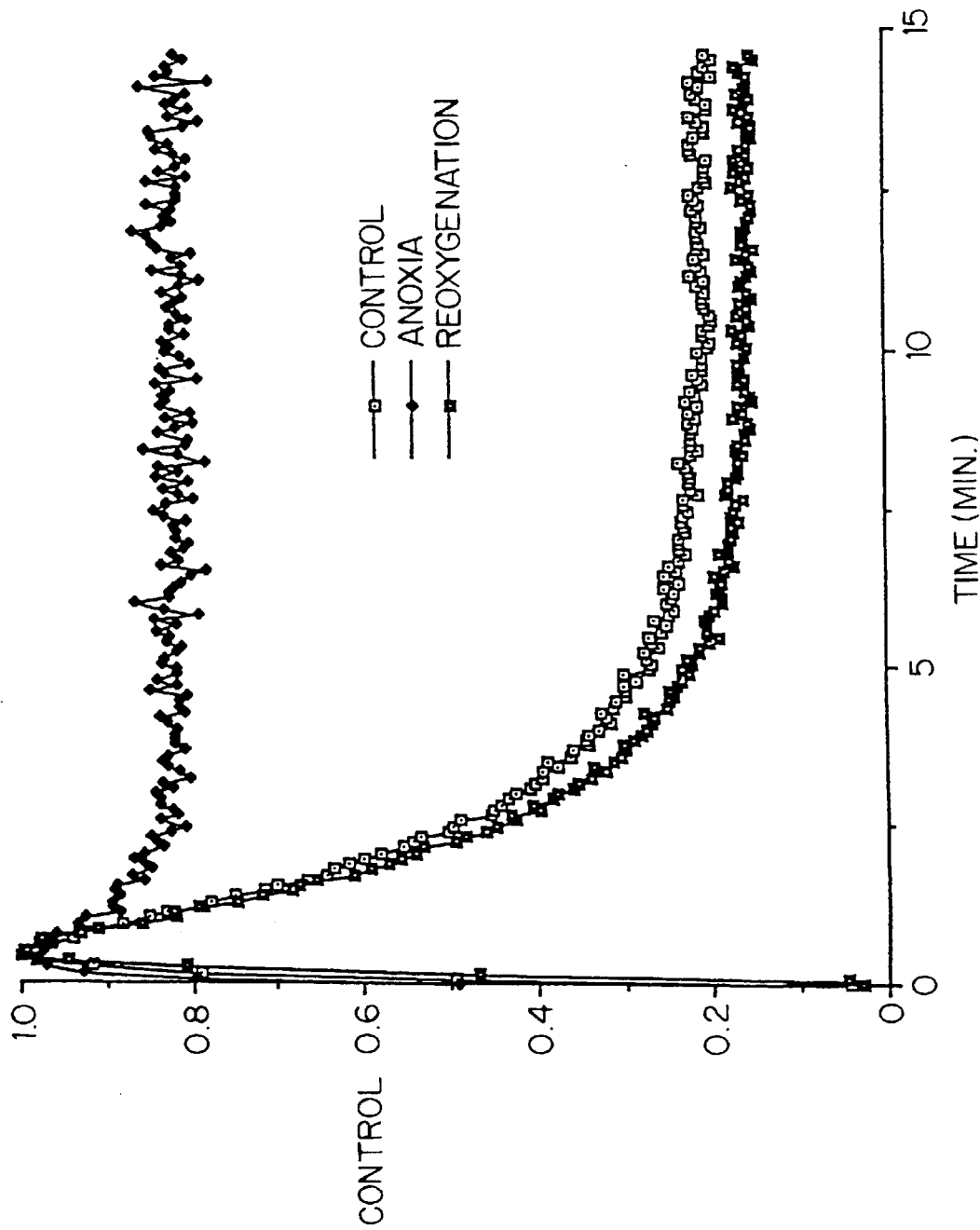
FIG. 2 is a graph demonstrating the effect of oxygen on the staying of Cu-62-ATSM in myocardia in the perfused myocardial model.
Figure 3:
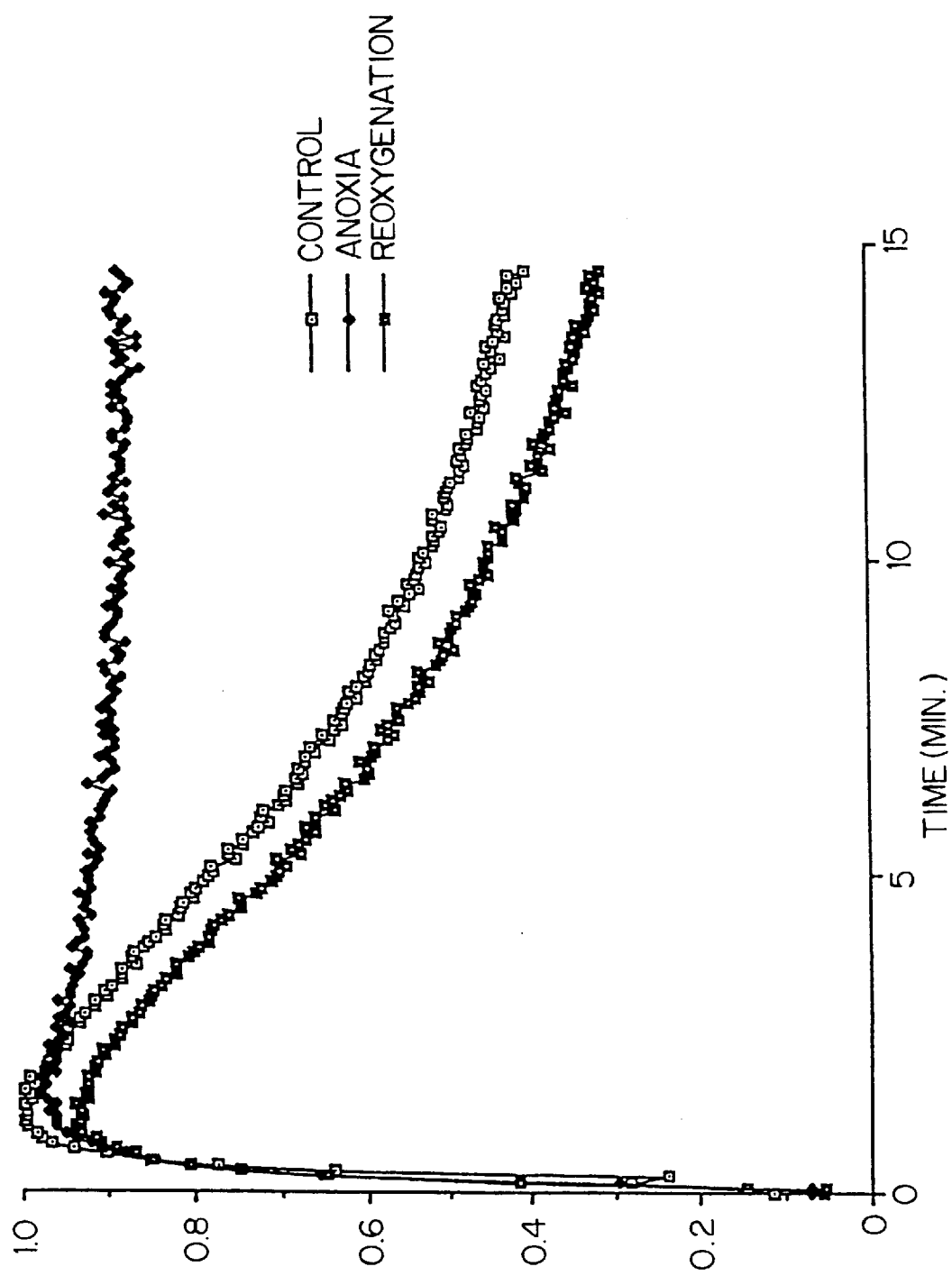
FIG. 3 is a graph demonstrating the effect of oxygen on the staying of Cu-62-PTSM2 in myocardia in the perfused myocardial model.
Figure 4:
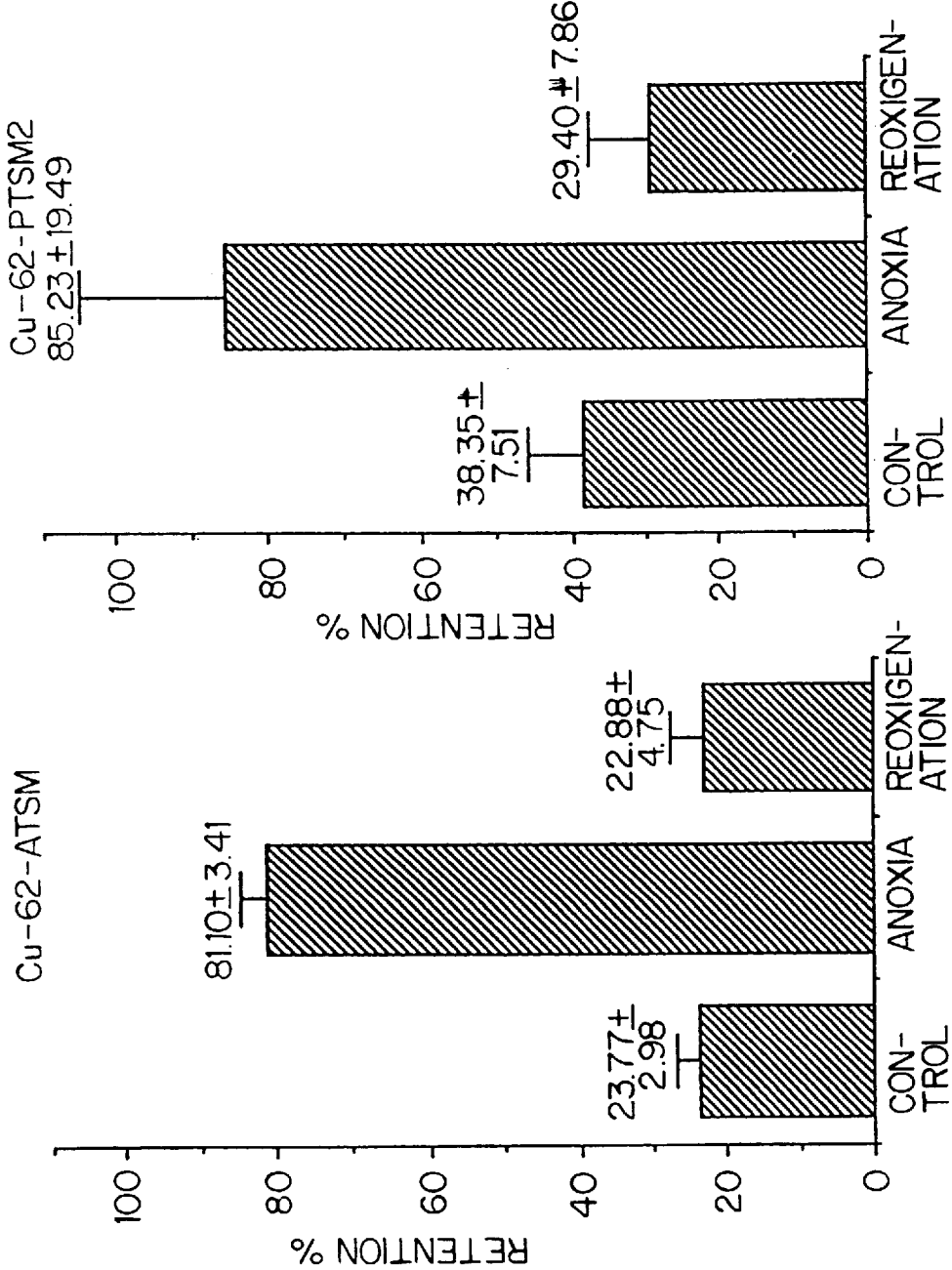
FIG. 4 is a bar graph demonstrating the effect of oxygen on the staying of Cu-62-ATSM and Cu-62 PTSM2 in myocardia in the perfused myocardia model.

FIG. 2 and FIG. 3 show the results relationg to Cu-62-ATSM and Cu-62-PTSM2 in the presence of oxygen (control), in the absence of oxygen (anoxia) and in the re-presence of oxygen (reoxygenation). Table 2 and FIG. 4 show comparisons of accumulation of Cu-62-DTS and Cu-62-DDS after 10 minutes of administration. In the presence of oxygen (control), Cu-62-ATSM rapidly disappeared from the myocardia and decreased down to about 20% of the maximum value after 10 minutes of administration. When the perfusate of the same perfused myocardial model was changed to an anoxic perfusate and after about 10 minutes Cu-62-ATSM was administered again, it stayed at a high level. Further, when the perfusate was changed back to the original one (reoxygenation) and Cu-62-ATSM was administered, it showed the same staying curve as that of the original trial. In the case of Cu-62-PTSM2 shown in FIG. 3, the rate of disappearance was slower as compared with Cu-62-ATSM but showed the same tendency after about 10 minutes of the administration.

Table 2 and FIG. 4 show the comparison of accumulation in the presence of oxygen (control), in the absence of oxygen (anoxia) and in the re-presence of oxygen (reoxygenation) after 10 minutes of administration. The rapid disappearance of all of the tested Cu-62-DTS and Cu-62-DDS from the tissue and the high accumulation and retention of those in the state of anoxia were observed clearly. From the results, it is revealed that there is clear difference in the extent of accumulation and retention of Cu-62-DTS and Cu-62-DDS in the tissue in the presence of oxygen and that in the absence of oxygen.

Example 3: Biodistribution of Cu-62-DTS and Cu-62-DDS

Each of Cu-62-DTS and Cu-62-DDS was administered to male ddY mice in caudal vein and anatomized with postmortem examination in time course. After isolating and weighing the blood and organs, each of the radioactivity contained in them was counted with a well-type scintillation counter and accumulation to each organ was calculated.

The results are shown in Tables 3–12. Each of Cu-62-DTS and Cu-62-DDS showed a characteristic accumulation behavior corresponding to the difference of their side chain. For example, Cu-62-PTSM showed a high transferability to brain and staying ability comparatively. However, it was revealed that Cu-62-ATSM, Cu-62-PTSM2, Cu-62-ATSM2 and so on were transferred once to brain but rapidly disappeared therefrom, indicating that they did not have staying ability in the normal animal brain. It is believed other Cu-62-DTS and Cu-62-DDS show same behavior with above one. This property is considered to be suitable for the detection of hypoxia in addition to the aforesaid ability of being reduced only in the electron excess state.

Since the diagnostic agent for hypoxia and mitochondrial dysfunction comprising a radioactive copper complex of dithiosemicarbazone derivative and a radioactive copper complex of diamine diol schiff base derivative according to the present invention has a good transferability to the target tissue, reduction reaction affinity at a hypoxic site, high stability in a nontarget site and rapid disappearance ability therefrom, it is very useful as a diagnostic agent for hypoxia and mitochondrial dysfunction in various organs and tissues such as brain, myocardia and the like.

TABLE 1

Effect of Rotenone-enhance on Copper Compound Reduction

| Cu complex | Control | Rotenone-enhance |
|---|---|---|
| Cu-PTSM | 48.8 ± 3.7 | 77.8 ± 2.9 |
| Cu-PTSM2 | 4.9 ± 2.1 | 15.3 ± 4.3 |
| Cu-ATSM | 3.4 ± 2.7 | 14.7 ± 3.4 |
| Cu-ATSE | 10.4 ± 4.7 | 24.5 ± 5.6 |
| Cu-ATSM2 | 4.3 ± 2.9 | 15.1 ± 5.4 |
| Cu-ETSE | 56.5 ± 7.3 | 76.6 ± 4.6 |
| Cu-DAED | 19.1 ± 2.7 | 30.8 ± 1.7 |

Note: % of reduced Cu

TABLE 2

Effect of oxygen on the retention of Cu-62-PTS and Cu-62-DDS in myocardia in the perfused myocardia model (after 10 minutes of administration)

| Cu-62-complex | Control | Anoxia | Reoxygenation |
|---|---|---|---|
| Cu-62-ATSM | 23.77 ± 2.98 | 81.10 ± 3.41 | 22.88 ± 4.75 |
| Cu-62-PTSM2 | 38.35 ± 7.51 | 85.23 ± 19.49 | 29.40 ± 7.86 |
| Cu-62-PTSM | 89.72 ± 4.01 | 98.88 ± 2.63 | 81.42 ± 14.03 |
| Cu-DAED | 55.65 ± 15.50 | 68.87 ± 19.12 | 43.37 ± 5.34 |

TABLE 3

Biodistribution of Cu-62-PTSM

| Tissue | 1 Minute | 5 Minutes | 30 Minutes |
|---|---|---|---|
| Blood | 4.01 (0.27) | 2.73 (0.27) | 1.48 (0.18) |
| Brain | 8.23 (1.37) | 7.15 (0.56) | 7.42 (1.01) |
| Heart | 21.64 (7.25) | 14.94 (1.39) | 14.62 (2.69) |
| Lung | 26.21 (6.43) | 22.26 (2.77) | 17.54 (1.31) |
| Liver | 5.35 (2.44) | 14.34 (2.18) | 23.99 (3.40) |
| Kidney | 12.75 (3.54) | 13.90 (1.63) | 12.08 (0.79) |
| Brain/Blood | 2.05 (0.29) | 2.64 (0.37) | 4.73 (0.40) |
| Heart/Blood | 5.36 (1.57) | 5.53 (0.99) | 8.42 (1.43). |

Note: % ID/g [tissue]
( ): standard deviation of average of 4 animals

TABLE 4

Biodistribution of Cu-62-ATSM

| Tissue | 1 Minute | 5 Minutes | 30 Minutes |
|---|---|---|---|
| Blood | 2.94 (0.51) | 1.42 (0.25) | 2.13 (0.29) |
| Brain | 6.01 (0.82) | 2.37 (0.30) | 2.81 (0.41) |
| Heart | 5.63 (1.19) | 2.10 (0.27) | 2.97 (0.44) |
| Lung | 36.00 (4.17) | 34.92 (8.11) | 13.12 (3.90) |
| Liver | 4.45 (0.47) | 10.61 (1.62) | 18.07 (3.33) |
| Kidney | 16.60 (1.37) | 12.76 (1.99) | 10.91 (1.19) |
| Brain/Blood | 2.06 (0.22) | 1.68 (0.11) | 1.33 (0.15) |
| Heart/Blood | 1.91 (0.18) | 1.49 (0.17) | 1.41 (0.18) |

Note: % ID/g [tissue]
( ): standard deviation of average of 4 animals

TABLE 5

Biodistribution of Cu-62-PTSM2

| Tissue | 1 Minute | 5 Minutes | 30 Minutes |
|---|---|---|---|
| Blood | 1.99 (0.35) | 1.50 (0.22) | 1.42 (0.37) |
| Brain | 5.16 (1.40) | 3.35 (0.48) | 1.58 (0.06) |
| Heart | 6.30 (1.56) | 2.04 (0.39) | 1.64 (0.20) |
| Lung | 26.15 (4.52) | 17.19 (3.36) | 11.45 (1.90) |
| Liver | 2.59 (0.50) | 11.34 (2.13) | 13.77 (2.90) |
| Kidney | 9.09 (1.31) | 3.96 (0.28) | 5.08 (0.68) |
| Brain/Blood | 2.57 (0.41) | 2.25 (0.28) | 1.19 (0.36) |
| Heart/Blood | 3.14 (0.35) | 1.36 (0.22) | 1.25 (0.49) |

Note: % ID/g [tissue]
( ): standard deviation of average of 4 animals

TABLE 6

Biodistribution of Cu-62-ATSM2

| Tissue | 1 Minute | 5 Minutes | 30 Minutes |
|---|---|---|---|
| Blood | 21.41 (7.15) | 2.78 (0.64) | 1.79 (0.38) |
| Brain | 1.82 (0.74) | 1.54 (0.39) | 0.50 (0.11) |
| Heart | 14.70 (7.87) | 2.64 (0.75) | 1.60 (0.27) |
| Lung | 85.75 (20.70) | 12.23 (5.48) | 7.37 (1.46) |
| Liver | 19.40 (6.41) | 30.70 (6.46) | 17.59 (1.35) |
| Kidney | 4.84 (1.36) | 3.77 (0.95) | 6.32 (1.06) |
| Brain/Blood | 0.08 (0.01) | 8.56 (0.13) | 0.28 (0.06) |
| Heart/Blood | 0.65 (0.65) | 0.95 (0.95) | 0.28 (0.91) |

Note: % ID/g [tissue]
( ): standard deviation of average of 4 animals

TABLE 7

Biodistribution of Cu-62-ETSM

| Tissue | 1 Minute | 10 Minutes | 20 Minutes |
|---|---|---|---|
| Blood | 5.35 (0.78) | 4.46 (0.30) | 2.94 (0.31) |
| Brain | 9.63 (0.63) | 9.79 (0.69) | 8.50 (1.17) |
| Heart | 18.64 (2.00) | 16.43 (0.96) | 12.10 (2.06) |
| Lung | 27.24 (2.63) | 28.95 (2.79) | 23.76 (4.70) |
| Liver | 10.17 (1.98) | 18.80 (1.23) | 17.95 (1.84) |
| Kidney | 25.27 (1.91) | 21.02 (1.49) | 15.17 (1.73) |

Note: % ID/g [tissue]
( ): standard deviation of average of 5 animals

TABLE 8

Biodistribution of Cu-62-ETSE

| Tissue | 1 Minute | 10 Minutes | 20 Minutes |
|---|---|---|---|
| Blood | 5.90 (0.62) | 3.92 (0.41) | 3.21 (0.62) |
| Brain | 9.99 (0.73) | 6.69 (0.77) | 5.88 (0.65) |
| Heart | 16.13 (1.40) | 8.43 (1.51) | 6.96 (0.96) |
| Lung | 17.95 (1.50) | 18.67 (2.35) | 16.71 (0.69) |
| Liver | 10.92 (1.47) | 21.37 (2.40) | 19.87 (2.52) |
| Kidney | 21.34 (1.14) | 15.76 (1.60) | 12.35 (1.97) |

Note: % ID/g [tissue]
( ): standard deviation of average of 5 animals

TABLE 9

Biodistribution of Cu-62-PTSE

| Tissue | 1 Minute | 10 Minutes | 20 Minutes |
|---|---|---|---|
| Blood | 4.89 (0.34) | 3.89 (0.48) | 2.56 (0.21) |
| Brain | 8.45 (0.77) | 8.28 (0.30) | 6.42 (0.73) |
| Heart | 13.24 (1.81) | 11.61 (1.58) | 8.48 (1.28) |
| Lung | 17.20 (1.80) | 23.14 (1.11) | 18.79 (3.36) |
| Liver | 8.78 (1.05) | 18.82 (2.63) | 16.97 (4.58) |
| Kidney | 19.80 (3.08) | 17.43 (1.93) | 13.23 (0.95) |

Note: % ID/g [tissue]
( ): standard deviation of average of 5 animals

TABLE 10

Biodistribution of Cu-62-ATSE

| Tissue | 1 Minute | 10 Minutes | 20 Minutes |
|---|---|---|---|
| Blood | 4.51 (0.41) | 2.78 (0.49) | 1.73 (0.10) |
| Brain | 7.54 (0.64) | 2.99 (0.55) | 1.59 (0.18) |
| Heart | 7.32 (0.76) | 3.42 (0.64) | 2.20 (0.34) |
| Lung | 40.42 (3.33) | 27.96 (1.46) | 20.52 (2.04) |
| Liver | 8.08 (2.16) | 16.93 (1.05) | 13.46 (1.79) |
| Kidney | 20.24 (1.78) | 12.62 (2.07) | 7.84 (1.13) |

Note: % ID/g [tissue]
( ): standard deviation of average of 5 animals

TABLE 11

Biodistribution of Cu-62-DSDP

| Tissue | 1 Minute | 10 Minutes | 20 Minutes |
|---|---|---|---|
| Blood | 16.03 (2.12) | 5.40 (0.77) | 3.09 (0.53) |
| Brain | 1.50 (1.19) | 0.69 (0.11) | 0.53 (0.03) |
| Heart | 8.32 (1.37) | 6.66 (0.92) | 5.01 (0.72) |
| Lung | 17.49 (1.63) | 21.49 (2.56) | 16.49 (3.43) |
| Liver | 14.61 (1.29) | 25.03 (0.57) | 24.42 (2.90) |
| Kidney | 19.76 (1.49) | 22.22 (1.48) | 15.71 (2.84) |

Note: % ID/g [tissue]
( ): standard deviation of average of 5 animals

TABLE 12

Biodistribution of Cu-62-DAED

| Tissue | 1 Minute | 10 Minutes | 20 Minutes |
|---|---|---|---|
| Blood | 16.03 (2.36) | 4.76 (0.60) | 3.42 (0.27) |
| Brain | 0.69 (0.11) | 0.52 (0.07) | 0.43 (0.06) |
| Heart | 7.36 (1.46) | 6.13 (0.46) | 4.99 (0.59) |
| Lung | 16.48 (2.44) | 20.19 (3.72) | 15.94 (2.25) |
| Liver | 14.78 (1.73) | 25.55 (3.27) | 22.48 (2.62) |
| Kidney | 19.64 (2.88) | 20.13 (2.04) | 15.36 (1.55) |

Note: % ID/g [tissue]
( ): standard deviation of average of 5 animals

What is claimed is:

1. A diagnostic agent for hypoxia or mitochondrial dysfunction comprising a radioactive copper complex of a dithiosemicarbazone derivative represented by the following formula:

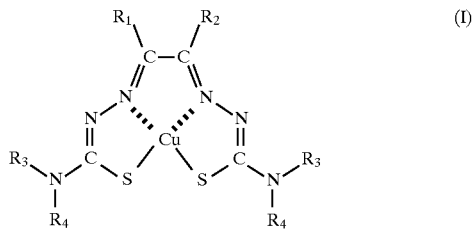

wherein each of $R_1$, $R_2$, $R_3$ and $R_4$ independently represents hydrogen, alkyl or alkoxy, with the proviso that $R_1$ and $R_2$ are the same, and Cu represents a radioactive isotope Cu-62, or a radioactive copper complex of a diamine diol schiff base derivative represented by the following formulae:

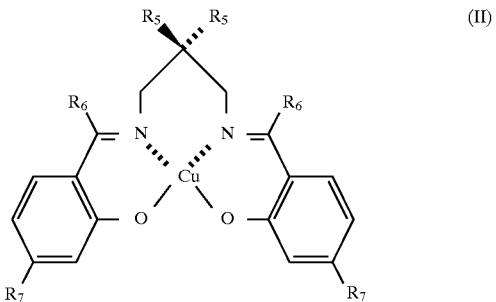

wherein each of $R_5$, $R_6$, and $R_7$ independently represents hydrogen, alkyl or alkoxy, and Cu represents a radioactive isotope Cu-62, or

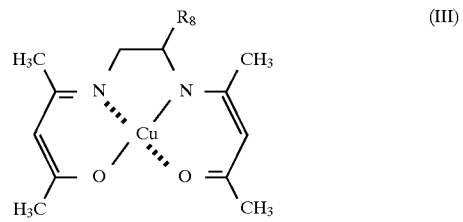

wherein the $R_8$ represents hydrogen or alkyl, and Cu represents a radioactive isotope Cu-62.

2. A diagnostic agent for hypoxia or mitochondrial dysfunction comprising a radioactive copper complex of a dithiosemicarbazone derivative represented by the following formula:

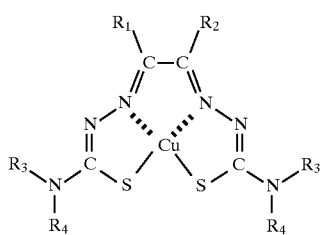

wherein each of $R_1$, $R_2$, $R_3$ and $R_4$ independently represents hydrogen, alkyl or alkoxy, with the proviso that $R_1$ and $R_2$ are the same, and Cu represents a radioactive isotope Cu-62.

3. A diagnostic agent for hypoxia or mitochondrial dysfunction comprising a radioactive copper complex of a diamine diol schiff base derivative represented by the following formula:

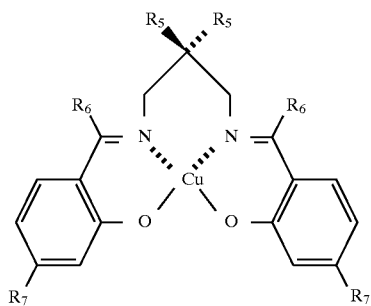

wherein each of $R_5$, $R_6$, and $R_7$ independently represents hydrogen, alkyl or alkoxy, and Cu represents a radioactive isotope Cu-62.

4. A diagnostic agent for hypoxia or mitochondrial dysfunction comprising a radioactive copper complex of a diamine diol schiff base derivative represented by the following formula:

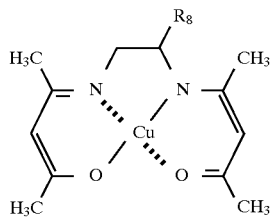

wherein the $R_8$ represents hydrogen or alkyl, and Cu represents a radioactive isotope Cu-62.

5. A diagnostic agent according to claim 1, wherein said radioactive copper complex of diamine diol schiff base derivative is Cu-62-disalicylaldehyde-2,2-dimethyl-1,3-propanediamine or Cu-62-diacetylacetone ethylenediamine.

6. A method of diagnosis of hypoxia or mitochondrial dysfunction which comprises administering an effective amount of a radioactive copper complex of a dithiosemicarbazone derivative or a radioactive copper complex of a diamine diol shiff base derivative according to claim 1, to a mammal and detecting the radioactive copper nuclide staying partially in the mammal body.

7. A method according to claim 6, wherein the radioactive copper complex of dithiosemicarbazone derivative is Cu-62-diacetyl bis(N4-methylthiosemicarbazone) or Cu-62-diacetyl bis(n4dimethylthiosemicarbazone).

8. A method according to claim 6, wherein the radioactive copper complex of diamine diol schiff base derivative is Cu-62-disalicylaldehyde-2,2-dimethyl-1,3-propanediamine or Cu-62-diacetylacetone ethylenediamine.

9. A method of diagnosing hypoxia or mitochondrial dysfunction using a radioactive copper complex of a dithiosemicarbazone derivative of a radioactive copper complex of a diamine diol schiff base derivative according to claim 1.

10. A diagnostic agent according to claim 2, wherein $R_4$ is methyl.

11. A diagnostic agent according to claim 1, wherein said radioactive copper complex of dithiosemicarbazone derivative is Cu-62-diacetyl bis (N4-methylthiosemicarbazone) or Cu-62-diacetyl bis(N4-dimethylthiosemicarbazone).

* * * * *